US010108085B2

(12) United States Patent
Peters et al.

(10) Patent No.: US 10,108,085 B2
(45) Date of Patent: Oct. 23, 2018

(54) METHOD FOR LOCALIZING DEFECTS ON SUBSTRATES

(71) Applicants: Carl Zeiss SMT GmbH, Oberkochen (DE); Carl Zeiss AG, Oberkochen (DE)

(72) Inventors: Jan Hendrik Peters, Radebeul (DE); Jörg Frederik Blumrich, Jena (DE); Dirk Seidel, Jena (DE); Christoph Husemann, Jena (DE)

(73) Assignees: Carl Zeiss SMT GmbH, Oberkochen (DE); Carl Zeiss AG, Oberkochen (DE)

( * ) Notice: Subject to any disclaimer, the term of this patent is extended or adjusted under 35 U.S.C. 154(b) by 126 days.

(21) Appl. No.: 15/400,221

(22) Filed: Jan. 6, 2017

(65) Prior Publication Data

US 2017/0115557 A1    Apr. 27, 2017

Related U.S. Application Data

(63) Continuation of application No. PCT/EP2015/065542, filed on Jul. 8, 2015.

(30) Foreign Application Priority Data

Jul. 8, 2014 (DE) .................. 10 2014 213 198

(51) Int. Cl.
*G03F 1/22* (2012.01)
*G03F 1/84* (2012.01)
*G01N 21/33* (2006.01)
*G01N 21/88* (2006.01)

(52) U.S. Cl.
CPC .............. *G03F 1/84* (2013.01); *G01N 21/33* (2013.01); *G01N 21/88* (2013.01); *G03F 1/22* (2013.01)

(58) Field of Classification Search
CPC .. G03F 1/22; G03F 1/84; G01N 21/33; G01N 21/88
USPC ...................................... 430/5, 30
See application file for complete search history.

(56) References Cited

U.S. PATENT DOCUMENTS

| | | |
|---|---|---|
| 2004/0016897 A1 | 1/2004 | Stokowski et al. |
| 2004/0165165 A1 | 8/2004 | Yun et al. |
| 2010/0153059 A1 | 6/2010 | Klose et al. |
| 2010/0254611 A1 | 10/2010 | Arnz |
| 2011/0018186 A1 | 1/2011 | Tsai |
| 2012/0063666 A1 | 3/2012 | Arnz et al. |
| 2012/0081712 A1 | 4/2012 | Laengle |
| 2012/0121205 A1 | 5/2012 | Arnz et al. |
| 2012/0238096 A1 | 9/2012 | Xiong et al. |
| 2012/0314910 A1 | 12/2012 | Arnz |
| 2013/0017475 A1 | 1/2013 | Terasawa et al. |
| 2013/0019212 A1 | 1/2013 | Seidel et al. |
| 2013/0245971 A1 | 9/2013 | Kusunose et al. |
| 2016/0138907 A1 | 5/2016 | Budach et al. |

FOREIGN PATENT DOCUMENTS

| | | | |
|---|---|---|---|
| DE | 102009015594 | 10/2010 | ............ G01B 11/03 |
| DE | 102010047051 | 3/2012 | ............... G06T 7/60 |
| DE | 102011077296 | 12/2012 | ............ G01B 11/14 |
| DE | 102013211403 | 12/2014 | ............... G03F 1/72 |
| JP | 2000-010013 | 1/2000 | ............ G02B 21/14 |
| JP | 2005-049663 | 2/2005 | ............... G03F 1/08 |
| WO | WO 2008/025433 | 3/2008 | ............... G01J 9/00 |
| WO | WO 2013/188232 | 12/2013 | ........... H01L 21/027 |

OTHER PUBLICATIONS

Japanese Office Action for Japanese Application No. 2017-500934 dated Jan. 30, 2018.
German Examination Report for German Application No. 10 2014 213 198.7 dated Jan. 30, 2015.
International Search Report for International Application No. PCT/EP2015/065542 dated Nov. 13, 2015.
Klose et al, "PROVE™ a Photomask Registration and Overlay Metrology System for the 45 nm node and beyond", Proc. of SPIE, vol. 7028, pp. 702832-1-702832-6 (2008).
Wang et al., "Zernike Phase Contrast Microscope for EUV mask inspection", *Proc. of SPIE*, vol. 9048, pp. 904810-1-904810-8.
Zhang et al., "Efficient Pattern Relocation for EUV Blank Defect Mitigation", *IEEE*, pp. 719-725 (2012).

*Primary Examiner* — Christopher G Young
(74) *Attorney, Agent, or Firm* — Fish & Richardson P.C.

(57) ABSTRACT

In a method for localizing defects on a substrate for EUV masks, a phase contrast optical unit having a phase mask is used for examining the substrate.

20 Claims, 12 Drawing Sheets

METHOD FOR LOCALIZING DEFECTS ON SUBSTRATES

CROSS REFERENCE TO RELATED APPLICATIONS

This application is a continuation of International Application PCT/EP2015/065542, having a filing date of Jul. 8, 2015, which claims priority to German patent application 10 2014 213 198.7, filed on Jul. 8, 2014. The entire contents of the above applications are hereby incorporated by reference.

TECHNICAL FIELD

The invention relates to a method for localizing defects on substrates for producing optical components of a microlithographic projection exposure apparatus, on substrates for lithography masks or on lithography masks. The invention furthermore relates to a method for producing EUV lithography masks. Furthermore, the invention relates to an apparatus for localizing defects on substrates.

BACKGROUND

During the production of lithography masks it is essential to ensure that the substrates from which the masks are produced have no defects. In the case of EUV masks, in particular, such defects can have the consequence that the mask cannot be used. An apparatus for inspecting EUV masks is known from US 2011/018186 A.

SUMMARY

In a general aspect, the invention improves a method for localizing defects on substrates, in particular a method for localizing defects on substrates for producing optical components of a microlithographic projection exposure apparatus, on substrates for lithography masks or on lithography masks.

In another general aspect, the invention includes using a phase contrast optical unit having a phase mask for inspecting a substrate. The invention provides for detecting a phase shift brought about by the substrate of the illumination radiation by use of a sensor device arranged in the beam path downstream of the phase mask.

The substrate can be, in particular, a substrate for producing a lithography mask, in particular an EUV mask. A semifinished product can be involved. The substrate can be unstructured. It may also already have been provided with a structure. The finished lithography mask, in particular the EUV mask, can also be involved. The substrate can also be a so-called mask blank, that is to say a substrate having an unstructured multilayer. The substrate can also be a substrate for producing an optical component, in particular a mirror, in particular an EUV mirror. For the sake of simplicity, just the term "substrate" is used hereinafter. This shall include all of the possibilities mentioned above, unless explicitly indicated otherwise.

According to the invention, it has been recognized that a large number of the defects of such substrates arise at the boundary layer between the base substrate and the multilayer applied thereon. Said defects can be made visible, in particular analyzed, in particular measured and/or localized, by use of a phase contrast method.

Defects between the base substrate and the multilayer arranged thereon are also referred to as buried defects, phase defects or embedded defects. The method serves in particular for analyzing, in particular for measuring and/or localizing such defects.

The base substrate is, in particular, a substrate composed of a material having a low thermal expansion (LTEM substrate; low thermal expansion material substrate). The base substrate can be composed in particular of quartz or a so-called ULE glass (Ultra Low Expansion glass) or comprise a proportion of such substances.

A multilayer comprising a sequence of molybdenum-silicon double plies is applied to the base substrate. The multilayer is designed in such a way that it results in a reflection of EUV radiation. A cover, in particular composed of ruthenium, can be applied to the multilayer.

The base substrate together with the multilayer and, if appropriate, the ruthenium cover and an unstructured absorber layer forms the actual substrate for the EUV mask, which is also referred to as EUV blank. The EUV blank can also comprise even further layers. Before the absorber layer is applied, the EUV blank is also designated as EUV blank semifinished product.

The method is described in particular in association with the production of EUV masks, in particular in association with EUV masks having structures for the lithographic structuring of wafers. This merely constitutes one specific application. Generally, the substrate and/or the EUV blank can also be used for other purposes. In particular, it can also be used for producing an EUV mirror. In this case, it is also referred to as an EUV mirror semifinished product, EUV mirror blank or simply as EUV mirror. In this case, the EUV blank preferably comprises no, at least no continuous, that is to say no closed, absorber layer.

The substrate, in particular the EUV blank can have a length and width in the range of 1 cm to 3 m, in particular in the range of 3 cm to 1 m, in particular in the range of 5 cm to 50 cm, in particular in the range of 10 cm to 20 cm. The thickness of the EUV blank is in the range of 500 μm to 5 cm, in particular in the range of 1 mm to 2 cm, in particular in the range of 2 mm to 1 cm, in particular in the range of 3 mm to 8 mm.

Other dimensions of the EUV blank are likewise possible.

In accordance with one aspect of the invention, the phase mask is arranged on the image side. It is arranged, in particular, in a pupil plane of the phase contrast optical unit.

In accordance with a further aspect of the invention, a stop is provided on the illumination side. The geometric design of the phase mask and that of the stop are adapted in particular to one another, in particular in such a way that an illumination of a perfect, that is to say defect-free, substrate has the consequence that the light source is imaged exactly onto the phase mask.

In accordance with a further aspect of the invention, the phase mask is designed in an annular fashion. The phase mask can also be designed in a circular fashion. In particular, π/2 phase mask is involved, that is to say a phase mask which leads to a phase shift of the illumination radiation by π/2.

The phase-shifting region of the phase mask can have a transmittance of at least 50%, in particular at least 70%, in particular at least 80%, in particular at least 90%, in particular at least 95%, in particular at least 97%, in particular at least 99%. It can in particular also have a transmittance of less than 100%, in particular less than 99%, in particular less than 97%, in particular less than 95%, in particular less than 90%, in particular less than 80%, in particular less than 70%. It is suitable in particular for an apodized phase contrast method.

In accordance with a further aspect of the invention, the illumination device comprises a radiation source for generating illumination radiation having a wavelength in the range of 100 nm to 300 nm, in particular in the range of 150 nm to 250 nm. In particular, a laser, in particular having a wavelength of 248 nm or 193 nm, can be involved. Such radiation sources are cost-effective. They do not require a vacuum for the propagation of the illumination radiation. Moreover, they make it possible to use a phase contrast optical unit which is designed for such wavelengths. The construction of the apparatus for carrying out the method is considerably facilitated as a result.

In accordance with a further aspect of the invention, the preparation steps for preparing the inspection of the substrate to be examined comprise determining a positioning of the substrate in a coordinate system of the phase contrast optical unit. In this case, in particular, predefined bearing points of a positioning device and/or measurement marks on the substrate serve as reference points.

The precise localization of the defects is simplified and improved as a result. Provision is made, in particular, for determining the positioning of the substrate in the direction of the beam path of the phase contrast optical unit and/or in a direction perpendicular thereto. In particular, at least one interferometer device serves for precisely determining the positioning, in particular the position of the positioning device of the substrate.

The positioning device can be displaced in particular with at least three, in particular with six, degrees of freedom. It is displaceable in particular in an actively controllable manner.

An interferometer device, in particular an Etalon, can be provided for monitoring the wavelength of the illumination radiation.

The measurement marks on the substrate define a coordinate system for the measurement of the substrate. They are arranged on the substrate in particular according to an industry standard, in particular in accordance with the SEMI-P48 standard.

An auxiliary optical unit can be provided for the coarse alignment of the substrate on the positioning device.

In particular, the alignment and/or tilting of the substrate can be determined in the preparation steps.

The positioning device comprises three bearing points, in particular, onto which the substrate is placed. Provision is made for taking account of a flexure of the substrate during the localization of the defects. Said flexure can be determined from known mechanical data of the substrate beforehand, in particular by way of a simulation, in particular in accordance with a finite elements method. The flexure of the substrate can also be determined experimentally, in particular interferometrically.

In accordance with one aspect of the invention, the phase contrast optical unit comprises an imaging optical unit, which is also designated as projection optical unit. The projection optical unit can have in particular a numerical aperture of at least 0.3, in particular at least 0.4, in particular at least 0.5, in particular at least 0.6, in particular at least 0.7, in particular at least 0.8.

Moreover, the phase contrast optical unit can comprise a magnifying optical unit. By using the magnifying optical unit, the image of the region to be examined can be adapted to the sensor device, in particular to the size of the sensor. The magnifying optical unit can be arranged in particular in the beam path upstream of the phase mask.

The total magnification of the projection optical unit and of the magnifying optical unit is at least 10, in particular at least 20, in particular at least 30, in particular at least 50, in particular at least 100, in particular at least 150, in particular at least 200, in particular at least 250.

In accordance with a further aspect of the invention, the sensor device comprises a CCD camera. The sensor device can comprise an image processing unit, in particular a processor for image processing. It is also possible to provide a separate image processing unit.

In accordance with a further aspect of the invention, the examination steps comprise predefining a region to be examined (ROI, Region of Interest) on the substrate. The region to be examined comprises the expected position of a defect. It is predefined with an accuracy that is more precise than the diameter of the field of view of the phase contrast optical unit. It is predefined in particular with an accuracy of better than 15 µm, in particular better than 10 µm, in particular better than 5 µm, in particular better than 3 µm, in particular better than 1 µm.

In accordance with a further aspect of the invention, provision is made for displacing the substrate, in particular by use of the positioning device, such that the region to be examined is centered relative to the field of view of the phase contrast optical unit. For this purpose, the substrate can be displaced by use of the positioning device depending on the expected position of a defect. This has the advantage that the region to be examined, in particular the expected positioning of the defect, is always situated at the same location relative to the phase contrast optical unit. As a result, the analysis is simplified and the precise localization of the defect is improved.

In accordance with a further aspect of the invention, provision is made, in particular, for the substrate to be displaced by use of the positioning device before the at least one image is recorded. It is displaced, in particular, in such a way that the region to be examined of the substrate is centered in the coordinate system of the phase contrast optical unit. In this case, the absolute value by which the substrate is displaced is known. It is thus possible to measure the defect relative to a coordinate system of the phase contrast optical unit and subsequently to transform the measurement values into the coordinate system of the substrate.

In this case, the substrate coordinate system can be defined in particular by at least three measurement marks. In particular, a flexure of the substrate can be taken into account during the displacement and/or coordinate transformation.

In accordance with a further aspect of the invention, the examination steps comprise capturing an image stack having at least two, in particular at least three, in particular at least four, in particular at least five, in particular at least six, in particular at least seven, images. The image stack comprises in particular in each case at least one intrafocal image and at least one extrafocal image.

The images of the image stack can have equidistant defocusings. Two adjacent images can have in particular in each case a defocus difference in the range of 10 nm to 100 nm, in particular in the range of 25 nm to 50 nm.

The analysis of the defect, in particular the measurement and/or localization of the defect is improved by recording an image stack.

According to the invention, it has been recognized that the recording of a single image of the defect may also suffice for the analysis thereof, in particular the measurement and/or localization thereof. With the method according to the invention, it is sufficient, in particular, to record a single image of the defect in the best focal position. Additional intra- or extrafocal images are not absolutely necessary.

It has been recognized, in particular, that no contrast inversion occurs with the method according to the invention. This means, in particular, that in the best focal position, too, a contrast different than 0 is discernible in the imaging of a phase defect. The contrast can have a maximum in particular in the best focal position.

In accordance with one aspect of the invention, the analysis steps comprise determining a best focal position.

The precision of the method is improved as a result.

In accordance with a further aspect of the invention, the analysis steps comprise a two-stage method in which, in a first stage, a defect position is determined for each image of an image stack and in which, in a second stage, the defect positions of the images are adapted to a best focal position.

In the first stage, in particular, firstly a best focal position can be determined. This can be done for example by adapting a contrast criterion. The subsequent determination of the defect position for each image of the image stack can then be carried out in particular by use of symmetry correlation.

In particular, a linear or a quadratic approach can be chosen for adapting the defect positions of the images to the respective best focal position.

In accordance with a further aspect of the invention, the defect position in the substrate coordinate system is determined with an accuracy of better than 100 nm, in particular better than 50 nm, in particular better than 30 nm, in particular better than 20 nm, in particular better than 10 nm, in particular better than 5 nm.

It has been found that the method according to the invention makes it possible to localize defects with a spherical equivalent volume diameter (SEVD) of less than 200 nm, in particular less than 100 nm, in particular less than 50 nm, in particular less than 30 nm and/or a height of less than 10 nm, in particular less than 5 nm, in particular less than 3 nm, in particular less than 2 nm, in particular less than 1 nm, in particular less than 0.5 nm with a reliability (triple standard deviation, "3σ-repeatability") of better than 50 nm, in particular better than 30 nm, in particular better than 10 nm, in particular better than 6 nm. In the case of a defect height of 5 nm, the triple standard deviation was in particular approximately 1 nm.

In accordance with one aspect of the invention, the substrate has an absorber layer when carrying out the examination steps.

The absorber layer serves in particular for blocking the reflection of EUV radiation. It can comprise in particular a material having a proportion of a tantalum compound, in particular tantalum nitride (TaN), tantalum boron nitride (TaBN) or tantalum silicon nitride (TaSiN).

The absorber layer can have a thickness in the range of a few 10 nm to a few 100 nm, in particular in the range of 44 nm to 108 nm.

The fact that the method is applicable to substrates having such an absorber layer, that is to say to EUV blanks after application of the absorber layer, makes it significantly more flexibly applicable.

In accordance with a further aspect of the invention, provision is made for the analysis and/or aftertreatment steps to comprise a reconstruction step for determining a phase image and a subsequent phase image evaluation.

According to the invention it has been recognized that phase images have a significantly higher edge steepness than intensity images. It has been recognized, in particular, that no contrast inversion occurs in the case of a phase image. In particular, in the region of the best focal position, the phase image has a contrast different than zero, in particular a contrast maximum. By analyzing a phase image, it is thus possible to improve the accuracy and reproducibility of the localization of the defects. By analyzing the phase images, it is possible, in particular, to reduce the number of required images in the focus stack to be analyzed, without the accuracy and/or reproducibility of the analysis of the defects being adversely affected as a result. The number of images in the focus stack can be in particular at most five, in particular at most three, in particular at most two, in particular exactly one. This leads to a considerable time saving.

For the reconstruction step for reconstructing a phase image from intensity measurements, what are suitable are, in particular, a phase determination by use of an iterative Fourier transformation algorithm, in particular a Gerchberg-Saxton algorithm, model-based phase determination algorithms, methods based on the transport of intensity equation, or Fourier ptychography methods.

In another general aspect, the invention includes improving a method for producing EUV lithography masks.

Implementations may include using a method which involves inspecting a substrate for producing the EUV lithography mask before the structuring by use of the preceding method and choosing and/or aligning the structure in such a way that defects on the substrate are covered by an absorber layer.

According to the invention, it has been recognized that the defects are unimportant for the further function of the mask, provided that they are hidden under the absorber layer. By targeted selection and/or alignment of the structure which is intended to be applied to the substrate in order to produce the EUV lithography mask, it is thus possible to use even substrates which are not completely free of defects, without this resulting in disadvantageous effects with regard to the function of said masks.

In accordance with one aspect of the invention, inspecting the substrate in order to localize defects is carried out after applying the absorber layer.

Inspecting the substrate in order to localize defects can also be carried out before applying the absorber layer.

The method according to the invention can be used in particular for the preclassification of substrates, in particular in association with examination in an aerial imaging metrology system (AIMS). It leads to a considerable time saving. The AIMS examination can be shortened in particular by more than 50%, in particular more than 70%, in particular more than 90%, in particular more than 95%.

Another general aspect of the invention includes improving an apparatus for localizing defects on substrates.

Implementations can include use of an apparatus comprising a phase contrast optical unit.

For details and advantages of this apparatus, reference should be made to the description above.

In accordance with one aspect of the invention, the apparatus comprises an illumination device for illuminating the substrate to be examined with illumination radiation, wherein the illumination radiation has in particular a wavelength in the range of 100 nm to 300 nm, in particular in the range of 150 nm to 250 nm. The illumination device can comprise in particular a laser, in particular an argon fluoride laser (ArF laser). It can comprise in particular a laser having a wavelength of 193 nm or 248 nm.

The phase contrast optical unit has in particular an annular stop, in particular a circular stop, on the illumination side. The stop and the phase mask are adapted to one another, as described above.

In accordance with one aspect of the invention, the phase contrast optical unit comprises a Bertrand optical unit, with which the image of the phase contrast stop can be imaged onto the CCD camera. This simplifies the lateral alignment of the phase stop relative to the illumination-side stop.

DESCRIPTION OF DRAWINGS

Further details and particulars of the invention and advantages thereof are evident from the following description of exemplary embodiments with reference to the figures. In the figures.

DETAILED DESCRIPTION

Figure 1:
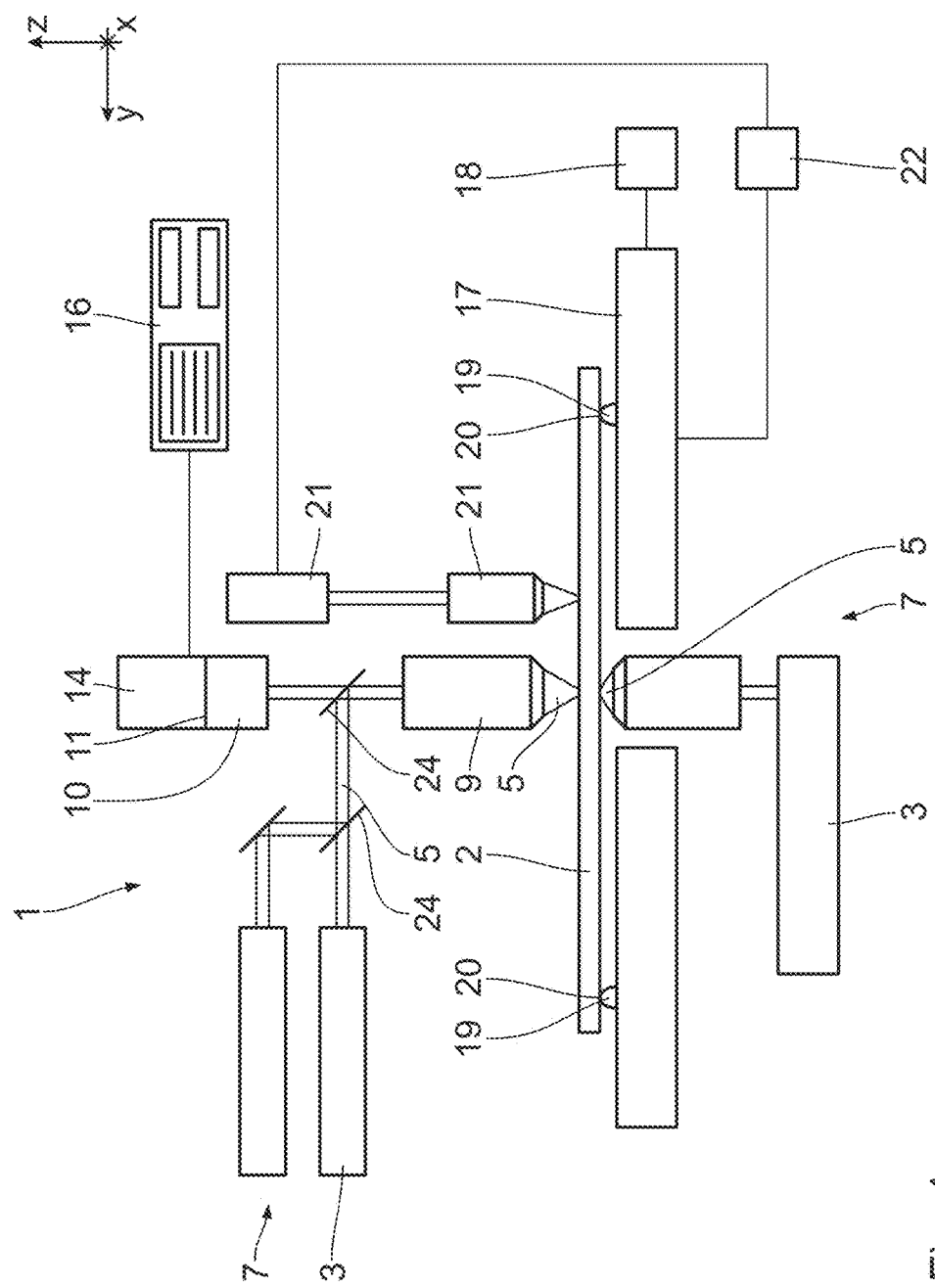
FIG. 1 schematically shows the construction of an apparatus for inspecting substrates, FIG. 2 schematically shows the beam path in an apparatus for inspecting substrates, FIG. 3 schematically shows the basic construction of a substrate for an EUV mask.

The general construction of an apparatus 1 for inspecting substrates, in particular for localizing defects on substrates, in particular on substrates for EUV masks, 2 is firstly described below with reference to FIG. 1.

The apparatus 1 comprises an illumination device 3. Two illumination devices 3 are illustrated in FIG. 1, wherein the upper illumination device 3 serves for illuminating the substrate 2 in the reflection mode. The lower illumination device 3 serves for illuminating the substrate 2 in the transmission mode. The apparatus 1 comprises at least one of these two illumination devices 3. It can also comprise both illumination devices 3. The flexibility of the apparatus 1 can be increased as a result. Two different illumination devices 3 make it possible, in particular, to use the apparatus 1 for inspecting different substrates 2.

The illumination device 3 comprises a radiation source 4. The radiation source 4 can be in particular a laser, in particular an ArF laser. The radiation source 4 serves for generating illumination radiation 5. The illumination radiation 5 has a wavelength of 193 nm.

Alternative radiation sources 4 which generate illumination radiation 5 having other wavelengths or in a different wavelength range are likewise possible.

The illumination device 3 may be part of an illumination system 7 comprising further optical components. The illumination system 7 can have, in particular, lens elements 6 and/or mirrors and/or filters and/or stops.

Figure 2:
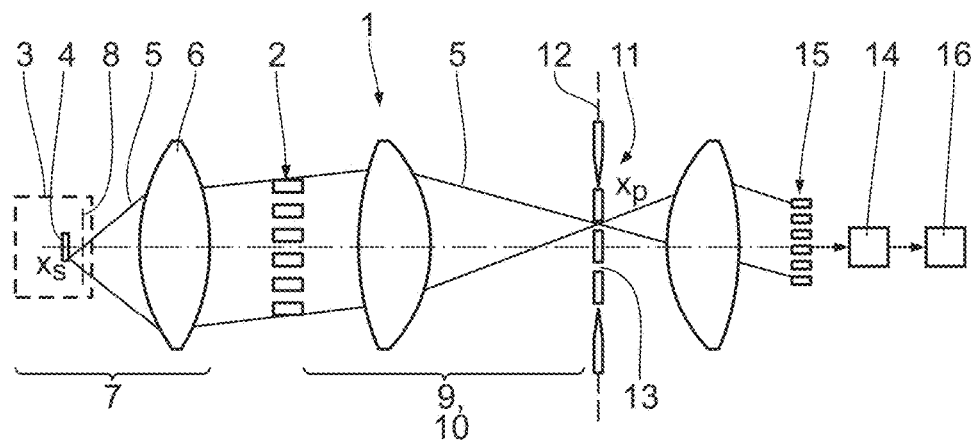

The lens element 6 illustrated in FIG. 2 should be understood to be by way of example. This component can also involve a plurality of lens elements and/or one or a plurality of mirrors.

The illumination system 7 can comprise a stop 8, in particular. The stop 8 is embodied in particular in a ring-shaped fashion, that is to say in an annular fashion. The stop 8 is arranged in particular in the region of the entrance pupil of the illumination system 7.

The substrate 2 is thus illuminated with a ring-shaped, that is to say annular, illumination setting.

The stop 8 defines in particular an illumination setting for illuminating the substrate 2.

A ring-shaped radiation source can also be used instead of a ring-shaped stop 8. As an alternative thereto, it is possible to arrange a multiplicity of point radiation sources in a ring-shaped region. As an alternative thereto, it is also possible to realize the ring-shaped illumination by use of a correspondingly switched micromirror array.

The illumination pupil for illuminating the substrate 2 has a radius $R_{ip}$.

The annular illumination which can be generated with the aid of the radiation source 4 and/or the stop 8 has an inner radius $r_{i0}$.

The annular illumination, in particular the stop 8, is described in even greater detail below.

Moreover, the apparatus 1 comprises an imaging optical unit 9. The imaging optical unit 9 has an object-side numerical aperture of 0.8. The imaging optical unit 9 is also referred to as a projection optical unit.

A magnifying optical unit 10 is arranged downstream of the imaging optical unit 9 in the beam path.

The imaging optical unit 9 and the magnifying optical unit 10 are parts of a phase contrast optical unit.

The total magnification of the imaging optical unit 9 and of the magnifying optical unit 10 is 265:1.

Moreover, the apparatus 1, in particular the phase contrast optical unit, comprises a phase mask 11. The phase mask 11 can be arranged in particular in a pupil plane 12 of the beam path of the illumination radiation 5. It can be arranged in particular in the beam path downstream of the magnifying optical unit 10.

The phase mask 11 is adapted to the shape of the illumination setting, in particular to the shape of the stop 8. It is embodied in particular in such a way that the stop 8 is imaged precisely onto the phase-shifting region 13 of the phase mask 11 if the substrate 2 to be examined is completely free of defects.

The phase mask 11 is embodied in particular in the shape of a circular ring, in particular in an annular fashion.

The apparatus 1 furthermore comprises a sensor device. The sensor device is embodied in particular as a camera, in particular as a CCD camera 14. An image 15 of the substrate 2 to be examined is recordable by use of the CCD camera 14. In particular, an image stack of the substrate 2 comprising at least two images having a different defocus is recordable by use of the CCD camera 14.

The CCD camera 14 is connected to an image processing device 16 in a data-transferring manner.

Furthermore, the apparatus 1 comprises a holding device 17. The holding device 17 serves for positioning the substrate 2 in the beam path of the inspection apparatus 1. The holding device 17 is actively controllable. It is precisely displaceable, in particular. It has six degrees of freedom of displacement. In particular, an interferometer device 18 is provided for determining the position and/or alignment of the holding device 17.

The holding device 17 comprises three supports 19. The supports 19 form bearing points 20 at which the substrate 2 bears on the holding device 17.

Furthermore, the apparatus 1 comprises an auxiliary optical unit 21. The auxiliary optical unit 21 is connected, in a data-transferring manner, to a control device 22 for controlling the displacement of the holding device 17. The substrate 2 can be coarsely aligned by use of the auxiliary optical unit 21.

Furthermore, the apparatus 1 comprises an autofocus system 23. In addition, one or more beam splitters 24 can be provided in the beam path of the apparatus 1.

The substrate 2 lies on the holding device 17 in particular in such a way that the side to be structured faces upwards. The substrate 2 bears on the supports 19 in particular by the side opposite to the side to be structured.

Moreover, the apparatus 1 can comprise an interferometer unit (not illustrated in the figures), in particular in the form of an etalon. The etalon serves for monitoring the wavelength of the illumination radiation 5. Variations of the wavelength which can occur on account of pressure, temperature or moisture fluctuations, for example, can be corrected with the aid of the etalon.

The substrate 2 to be examined is described in greater detail below with reference to FIGS. 3 and 4.

The substrate 2 comprises a base substrate 25. The base substrate 25 is composed of a material having a low coefficient of thermal expansion (LTEM material; low thermal expansion material substrate). This can involve, in particular, quartz or a so-called ULE glass (Ultra Low Expansion glass). The substrate has a length l, and a width w. The length l and the width w are 152 mm, for example. Other dimensions of the substrate 2 are likewise possible. The base substrate 25 has a thickness d. The thickness d of the substrate 2 can be 6.35 mm. Other thicknesses are likewise possible.

A multilayer 26 is applied to the base substrate 25. The multilayer 26 comprises a sequence of at least 10, in particular 20, in particular 30, in particular 40, in particular 50, silicon-molybdenum double plies. The number of silicon-molybdenum double plies is in particular less than 200, in particular less than 100. It can be in particular less than 80, in particular less than 70, in particular less than 60. In this case, each double ply comprises a silicon ply having a thickness of 4.1 nm and a molybdenum ply having a thickness of 2.8 nm. The multilayer 26 serves, in particular, for reflecting EUV radiation. A covering layer 27 is applied to the multilayer 26. The covering layer 27 can be composed of ruthenium. It has a thickness of 2.5 nm.

An absorber layer 28 is applied to the covering layer 27. The absorber layer 28 can comprise, in particular, materials comprising a proportion of a tantalum nitride compound, in particular tantalum nitride, tantalum boron nitride or tantalum silicon nitride.

The absorber layer 28 has a thickness in the range of 44 to 108 nm.

An antireflective coating 29 (ARC) is applied to the absorber layer 28. The antireflective layer 29 can be composed of the same base material as the absorber layer 28. Usually an oxygen gradient between the absorber layer 28 and the antireflective layer 29 is present in such a way that the oxygen proportion of the antireflective layer 29 is higher than that of the absorber layer 28. The antireflective layer 29 can comprise, in particular, a proportion of tantalum oxynitride.

Finally, a rear-side layer 30 is applied on the rear side of the base substrate 25, that is to say on the opposite side of the base structure 25 relative to the multilayer 26. The rear-side layer 30 is composed of an electrically conductive material. In particular, a coating of chromium can be involved. The rear-side layer 30 has a thickness in the range of 20 to 200 nm.

The totality of the layers 25 to 30 is also designated as EUV blank. It forms the substrate 2 for producing an EUV mask.

It has been established that, in particular, the boundary layer between the base substrate 25 and the multilayer 26 is crucial for the quality of the EUV mask produced from the substrate 2. It is assumed that more than 90% of defects 31 of the later EUV mask originate at said boundary layer. Such defects 31 can have the effect that the lithography mask produced from the substrate 2 is no longer used for the structuring of a wafer.

Furthermore, it has been established that the defects 31 on the surface of the base substrate 25 are covered during the deposition of the multilayer 26. They are visible as a phase defect, however. They are visible as a phase defect in particular during the irradiation of the mask with EUV radiation, in particular in the reflected portion of the EUV radiation.

Figure 4:
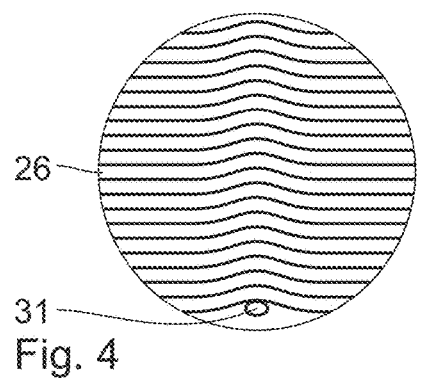
FIG. 4 shows an enlarged excerpt from the region IV of the cross section of the substrate in accordance with FIG. 3, FIGS. 5 to 8 show schematic flow charts of different variants of methods for producing EUV lithography masks.

For clarification, FIG. 4 illustrates how one of the defects 31 leads to a so-called bump defect in the multilayer 26. In general, a defect 31 leads to a deviation of the surface of the base substrate and/or of the multilayer 26 from a perfectly planar formation.

The so-called spherical equivalent volume diameter (SEVD) serves for characterizing the size of the defect 31.

Table 1 indicates an overview of critical defect sizes with respect to specific nodes. In this case, a node denotes half the line spacing on the wafer to be structured. The critical defect size is indicated as SEVD on the substrate 2.

TABLE 1

| Node [nm] | Critical defect size [nm] |
|---|---|
| 32 | 25.6 |
| 22 | 17.6 |
| 16 | 12.8 |
| 11 | 8.8 |

The defects 31 can be very flat. They can have a height of less than 1 nm. The height of the defects 31 is, in particular, in the range of 0.5 nm to 10 nm.

According to the invention, it has been recognized that a critical defect 31, that is to say a defect 31 that is large enough to have a possibly disadvantageous effect on the structuring of a wafer, must firstly be identified and secondly be repaired or compensated for.

For defects 31 which occur at the boundary between the base substrate 25 and the multilayer 26 or within the multilayer 26, conventional strategies which process the surface of the substrate 2 are not suitable for repair or compensation. The invention provides for hiding such defects 31 under the absorber layer 28. For this purpose, provision is made for choosing and/or aligning the structure with which the substrate 2 is intended to be structured in such a way that the defects 31 on the substrate 2 are covered by the absorber layer 28 even after the structure has been applied.

For this purpose, it is necessary to determine the exact position of the defects 31 on the substrate 2.

The below-described method for localizing defects on substrates 2 for EUV masks serves in particular for measuring such defects 31, in particular for precisely localizing the latter, in particular relative to measurement marks 32 (fiducial marks) which are applied to the substrate 2, in particular in a standardized manner, in particular in accordance with the SEMI P48 standard.

In particular, at least three measurement marks 32 are applied to the substrate 2. The measurement marks 32 define a substrate coordinate system.

If the positions of all the defects 31 of a substrate 2 are known, it is possible to create a substrate map with these positions. The mask design can subsequently be adapted to said map, in particular by a linear displacement and/or a rotation of the design, in such a way that at least a proportion of the defects 31 are covered by the absorber layer 28. It is possible, in particular, to adapt the mask design in such a way that at least 50%, in particular at least 70%, in particular at least 80%, in particular at least 90%, in particular at least 95%, in particular at least 99%, in particular all, of critical defects 31 are covered by the absorber layer 28. The defects 31 are covered by the absorber layer 28 in particular at least to such an extent that they no longer have a disadvantageous effect on the structuring of a wafer. If this is not possible, the substrate 2 can be segregated.

Different method sequences for producing EUV lithography masks, in particular for structuring the substrate 2, are described below. The different variants differ in particular in respect of at what point in time in the method sequence the substrate 2 is subjected to an inspection for localizing the defects 31. This may depend, in particular, on who carries out this inspection. In this case, a distinction is drawn, in particular, between the manufacturer and/or distributor of the substrate 2 ("blank supplier") and the distributor of the finished masks ("mask shop").

Figure 5:
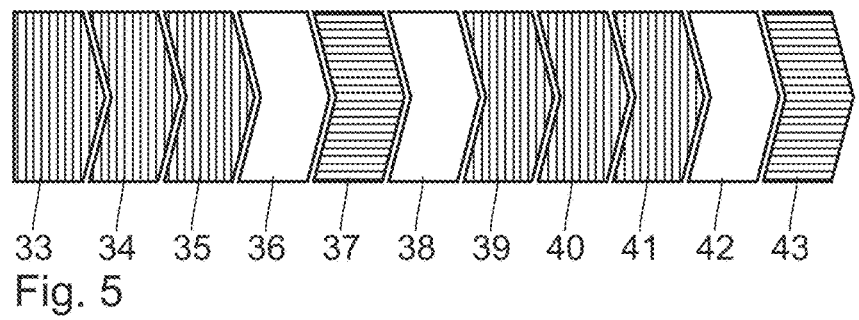

In the method sequence illustrated in FIG. 5, the apparatus 1 for localizing defects on the substrate 2 is not available to the supplier of the substrate 2. Moreover, it is assumed that the measurement and/or localization of the defects 31 are/is intended to take place before the absorber layer 28 is applied to the covering layer 27.

In a first deposition step 33, the multilayer 26 and the covering layer 27 are applied to the base substrate 25. In a subsequent marking step 34, the measurement marks (fiducial marks) are applied to the substrate 2.

In a subsequent inspection step 35, the multilayer 26 is examined.

The substrate 2 is then sent to the mask distributor in a first sending step 36.

In a subsequent localizing method 37, the defects 31 are measured, in particular localized. In a second sending step 38, the substrate 2 is sent back to the manufacturer.

In a subsequent second deposition step 39, the absorber layer 28 is deposited on the covering layer 27.

Afterward, a second inspection step 40 is provided for inspecting the absorber layer 28.

In a subsequent cleaning and final inspection step 41, the substrate 2 is cleaned and inspected once again.

It is then sent back to the mask distributor in a third sending step 42.

There, in a structuring step 43, it is finally provided with a structure for producing the EUV mask, wherein the structure is chosen and/or aligned in such a way that the defects 31 on the substrate 2 remain covered by the absorber layer 28.

In order to clarify the different process stations, the method steps 33 to 35 and 39 to 41 carried out by the manufacturer of the substrate 2 are identified by vertical hatchings in FIGS. 5 to 8. The process steps 37 and 43 carried out by the mask distributor are identified by horizontal hatchings.

Figure 6:
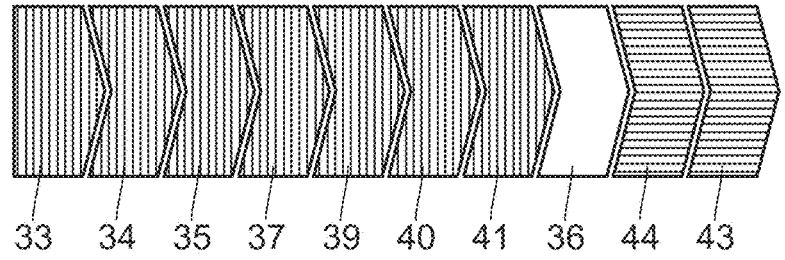

FIG. 6 illustrates the corresponding method sequence for the case where the localizing method 37 can be carried out by the manufacturer of the substrate 2. Two sending steps 38, 42 can be dispensed with in this case. Only the first sending step 36 is necessary. The latter can take place after the cleaning and final inspection step 41.

Before the structuring step 43, an inspection step 44 for inspecting the EUV blank is also provided at the mask distributor in this case.

Figure 7:
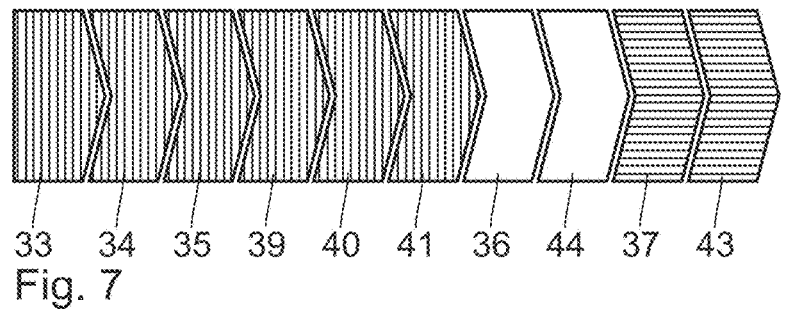

FIG. 7 illustrates the method sequence for the case where the localizing method 37 is not carried out by the manufacturer of the substrate 2, but the defects 31 are localized only after the second deposition step 39 for depositing the absorber layer 28. In this case, it is possible to carry out the localizing method 37 between the inspection step 44 and the subsequent structuring step 43.

Figure 8:
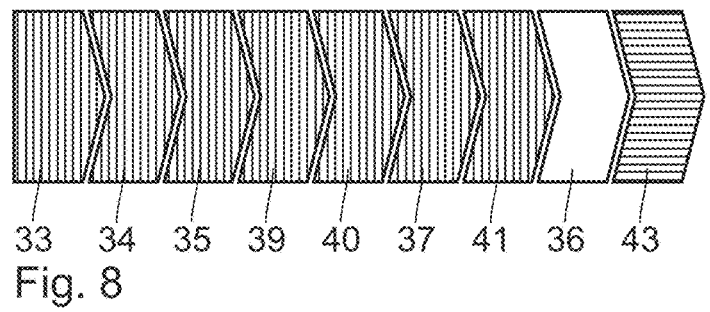
Figure 10:
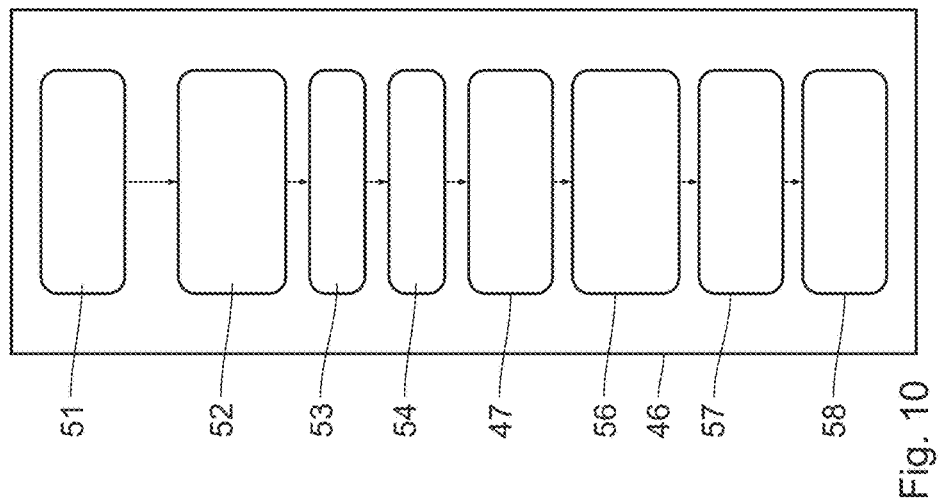
FIG. 10 shows a schematic illustration of the examination steps for examining the substrate.

FIG. 8 illustrates the case where the manufacturer of the substrate 2 carries out the localizing method 37, specifically after the second deposition step 39 for depositing the absorber layer 28. In this case, only the structuring step 43 has to be carried out by the mask distributor.

The localizing method 37 for localizing the defects 31 on the substrate 2 is described in greater detail below.

Generally, the localizing method 37 comprises preparation steps 45 for preparing the inspection of the substrate 2 to be examined, examination steps 46 for examining the substrate 2 and analysis and/or aftertreatment steps for processing and handling the signals captured by use of the CCD camera 14. The analysis and/or aftertreatment steps are referred to hereinafter as image analysis 47 for short.

Figure 9:
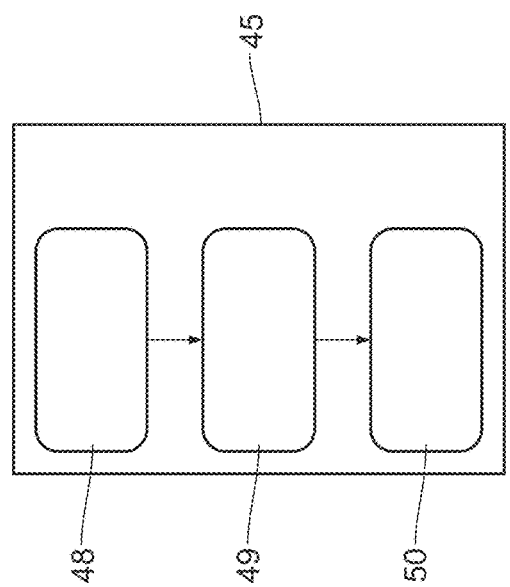
FIG. 9 shows a schematic illustration of the preparation steps for preparing the inspection of a substrate.
Figure 11:
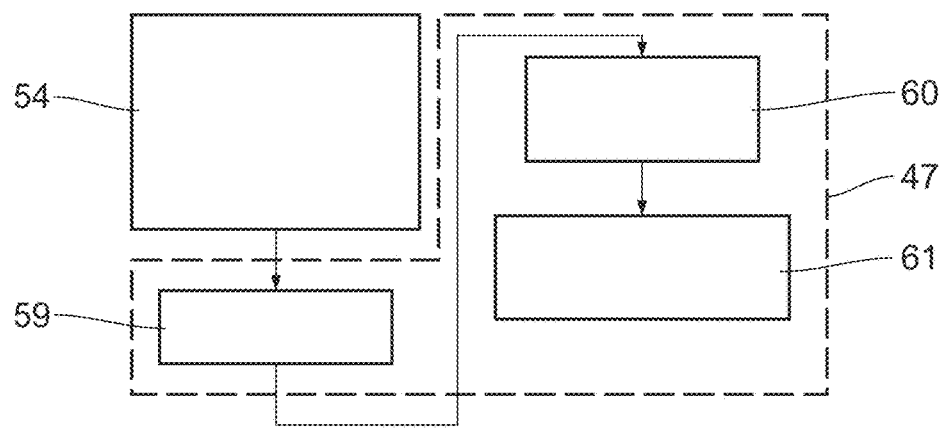
FIG. 11 shows a schematic illustration of the analysis steps for examining the substrate.

The preparation steps 45 are illustrated schematically in FIG. 9. They comprise an introduction step 48, in which the substrate 2 to be examined is introduced into the apparatus 1. A specific storage and introduction unit can be provided for this purpose. It is possible, in particular, to store a plurality of substrates 2 to be examined in such a unit. They can be introduced successively into the apparatus 1. The substrates 2 can be applied to the holding device 17 in particular in an automated manner from the storage unit.

A Cartesian coordinate system is used below in order to simplify positional designations. In this case, the z-direction represents the direction of a principal ray of the illumination radiation 5. The xy-plane is perpendicular thereto. It is substantially parallel to the holding device 17 and to the substrate 2 to be examined, provided that the flexure thereof is disregarded. The x- and y-directions are in particular parallel to the side edges of the substrate 2.

The substrate 2, after being applied to the holding device 17, in particular after being placed onto the supports 19, is adjusted in a first adjusting step. The first adjusting step 49 serves in particular for adjusting the substrate 2 in the z-direction.

In particular, the autofocus system 23 is provided for carrying out the first adjusting step 49. The substrate 2 is adjusted in the z-direction at least three points with the aid of the autofocus system 23. From these data, it is possible to determine the position of the substrate 2 in the z-direction, in particular an offset and a tilting of the substrate 2 on the holding device 17.

In a second adjusting step 50, the substrate 2 is adjusted in the x- and y-directions. The measurement marks 32 on the substrate 2 serve as a reference system for the adjustment in the x- and y-directions. From the data acquired in the two adjusting steps 49 and 50, it is possible to derive a substrate coordinate system which serves as a reference for the subsequent measurements, in particular localizations, of the defects 31.

Once the substrate 2 has been arranged on the holding device 17 and aligned, in particular adjusted, the actual examination steps 46 for measuring the defects 31, in particular for localizing the latter, can be carried out. The subsequent sequence of the examination steps 46 can be started and/or carried out manually. It can also be carried out in an automated manner. It can be started and/or controlled in particular by use of a control device, in particular by use of a script.

Firstly, a nominal, expected position of one of the defects 31 is predefined in a predefining step 51. The expected position of the defect 31 is predefined in particular in the substrate coordinate system which is predefined in particular by the measurement marks 32. The nominal position of the defects 31 is known from a previous inspection step in which the complete EUV blank is scanned. A positional accuracy of the position of the defects 31 of a maximum of 200 nm to 300 nm can be achieved in said inspection step.

The nominal position of the defects 31 can be determined in a separate method. In this case, the nominal positions of the defects 31 can be stored and retrieved in the present method. As an alternative thereto, it is also possible to determine the nominal positions of the defects 31 in an inspection step in the present method.

The nominal value of the position of the defect 31 is predefined with an accuracy which is considerably smaller, that is to say more accurate than the field of view of the imaging optical unit 9. Said field of view can have in particular a diameter of 15 μm or less. Advantageously, the nominal position of the defect 31 is predefined with an accuracy of better than 1 μm.

A region 62 to be examined (ROI, region of interest) can be predefined for the further method. The region to be examined is predefined in particular with an accuracy that is more precise than the diameter of the field of view of the imaging optical unit 9, in particular more precise than 15 μm, in particular more precise than 10 μm, in particular more precise than 5 μm, in particular more precise than 3 μm, in particular more precise than 1 μm.

In a subsequent z-compensation step 52, the substrate 2 is shifted in the z-direction with the aid of the holding device 17 in order to compensate for the flexure of the substrate 2 at the nominal position of the defect 31. In a displacement step 53, the substrate 2 is then displaced with the aid of the holding device 17 and the control device 22 in such a way that the region 62 to be examined, in particular the defect 31, is centered in the beam path of the imaging optical unit 9.

The image capture 54 can then start.

The image capture 54 comprises the recording of an autofocus image for focusing the defect 31. In addition, a focus stack with different, predefined, discrete defocusings is recorded. In particular, at least one intrafocal image and at least one extrafocal image are recorded. Provision can be made, for example, for recording an image stack with seven successive images, the defocus of which differs in each case by 30 nm.

The image stack can also have a different number of images. It can have in particular also fewer than seven images, in particular at most five images, in particular at most three images, in particular exactly one image. It can comprise in particular an image in the best focal position.

The image analysis 47 for determining the position of the defect 31 in the recorded images is then provided. The image analysis 47 can be carried out with the aid of the image processing device 16. This can be done in particular online or else offline.

In the image processing device, the recorded image stack is analyzed and the position of the defect 31 at the best focus is calculated.

Since the images are captured in the coordinate system of the imaging optical unit 9, but the displacement of the holding device 17 is known in the z-compensation step 52 and respectively in the displacement step 53, the positions of the defect 31 that are determined from the images can be transformed into the substrate coordinate system in a first correction step 56, in which the position of the holding device 17 is taken into consideration, and in a second correction step 57, in which the flexure of the substrate 2 is taken into account.

The position of the defect 31 or of the defects 31 of the substrate 2 is stored in a storage step 58.

The sequence of the examination steps 46 and of the image analysis 47 can be run through a number of times. It can be run through in particular as often as until all the defects 31 on the substrate 2 have been measured. It can also be run through as often as until the entire surface of the substrate 2 has been measured.

In principle, a plurality of defects 31 can be measured, in particular localized, simultaneously in a pass of the sequence of the examination steps 46.

The image capture 54 is described in greater detail below. As has already been described with reference to FIGS. 1 and 2, the method for localizing the defects 31 on the substrate 2 with the aid of the apparatus 1 provides for focusing an annular radiation source 4 or a stop 8 arranged in the entrance pupil of the illumination system 7 onto the substrate 2, in particular the defect 31. In the exemplary embodiment described by way of example, the radiation source 4 generates an illumination radiation 5 having a wavelength of 193 nm. The substrate 2 is examined in the reflection mode. It can be assumed to a first approximation that the illumination radiation reflected from the substrate 2 has a phase which is proportional to the height distribution on the substrate 2. In the case of a perfectly planar substrate 2, the reflected illumination radiation 5 has the same identical phase over the entire surface of the substrate 2. Defects 31, in particular bumps or pits, lead to corresponding distortions of the wavefront.

The reflected illumination radiation 5 is detected by using the sensor device embodied as a CCD camera 14.

The phase mask 11 is arranged in the beam path of the imaging optical unit 9 on the image side with respect to the substrate 2. The phase mask 11 is arranged in the beam path downstream of the magnifying optical unit 10. It is arranged in particular in a pupil plane of the beam path of the phase contrast optical unit.

The phase mask 11 is a π/2 phase mask. The illumination radiation 5 thus experiences a phase shift by π/2 upon passing through the phase mask 11.

The phase mask 11 has dimensions which are adapted to those of the ring-shaped radiation source 4 or of the stop 8. This should be understood to mean that the radiation source 4, in the case of a perfect, fault-free reflection at the completely defect-free substrate 2, is imaged exactly onto the phase mask 11, and vice versa. The illumination radiation 5 circulating directly from the radiation source 4 to the phase mask 11, that is to say the illumination radiation 5 which reaches the phase mask 11 in a manner free of diffraction, is thus shifted by π/2 phases by the phase mask 11. The diffracted illumination radiation 5 does not impinge on the phase-shifting region of the phase mask 11 and remains unchanged. An interference of the diffracted and undiffracted portions of the illumination radiation 5 thus occurs. This in turn makes it possible to determine the phase distribution of the wavefront by using a detector, in particular by using the CCD camera 14.

It has been found that annular embodiments of the radiation source 4 or of the stop 8 and of the phase mask 11 are advantageous for a high contrast-to-noise ratio.

In order to optimize the signal-to-noise ratio, it is possible to optimize the exact shape of the radiation source 4 or of the stop 8 and of the phase mask 11. Provision is made, in particular, for adapting the shape of said elements to the filling factor of the illumination pupil, that is to say the size of the radiation source 4, and/or the expected height distribution of the phase defect to be detected, in particular the curvature thereof.

For flat defects 31, in particular defects 31 having a height of less than 5 nm, in particular less than 3 nm, in particular less than 2 nm, in particular less than 1 nm, in particular less than 0.5 nm, and a high degree of filling, a ring-shaped illumination having an inner radius $r_{i,0}$ is provided, whose ratio to the radius $R_{ip}$ of the illumination pupil is in the range of 0.4 to 0.5. The outer radius of the illumination is determined by the degree of filling of the illumination pupil.

Correspondingly, the phase mask 11 has in the image-side aperture an inner radius $r_{a,0}$ whose ratio to the radius $R_{ap}$ of the image-side aperture is in the range of 0.4 to 0.5.

For defects 31 having a greater curvature and/or an illumination pupil having a lower degree of filling, an illumination of the substrate 2 to be examined with an inner radius $r_{i,0}=0$ is optimal. Here, too, the outer radius is determined by the degree of filling of the illumination pupil. In this case, the phase mask 11 also has an inner radius $r_{a,0}=0$.

Individual steps and details of the image analysis 47 are described in greater detail below.

Firstly, the best focal position is determined from the recorded image stack in a focus determining step 59. This can be done by matching a contrast criterion, for example over the sum of the squares of the deviations of adjacent pixels, to different z-positions of the holding device 17. In the case of a defocus in the range of less than 1 Rayleigh length, a parabolic fit is advantageous.

The position of the defect 31 is then determined in an individual image analysis 60 for each image of the image stack. For this purpose, in particular, the region 62 to be examined (ROI) is analyzed for each of the images with different defocus positions.

In order to determine the position of the defect 31, use is made of, in particular, a correlation method, in particular a symmetry correlation method, which is described in even greater detail below. However, alternative methods are likewise possible.

In a subsequent interpolation step 61, the values determined for the different images with different defocus positions are transformed from the respective defocus position into the best focal position. This can be carried out by using an adapting method, in particular with a linear or a quadratic approach. A common value for characterizing the position and/or the extents of the defect(s) 31 is finally determined from the different values.

It was possible to show that this image analysis 47 is robust with respect to the expected background noise, even in the case of defects 31 having a low signal-to-noise ratio.

Various methods for determining the position of a defect 31 in a camera image are known from the prior art. In this regard, reference should be made to US 2010/153059 A, US 2010/254611 A, US 2012/121205 A and US 2012/063666 A. It has been recognized that correlation-based methods which take account of all the pixels of the region to be examined (ROI) are advantageous in the case of images having low contrast and/or a low signal-to-noise ratio. One preferred method for the individual image analysis 60 is a so-called symmetry correlation method or the so-called symmetry correlation algorithm, which is described in even greater detail below. For details of this symmetry correlation method, reference should be made to DE 10 2010 047 051 A1, which is hereby fully incorporated in the present application as part thereof.

To a first approximation, it can be assumed that small defects 31 are symmetrical in relation to their position on the substrate 2. It has been recognized that a symmetry correlation method is therefore advantageous for determining the position of such a defect 31.

Figure 19:
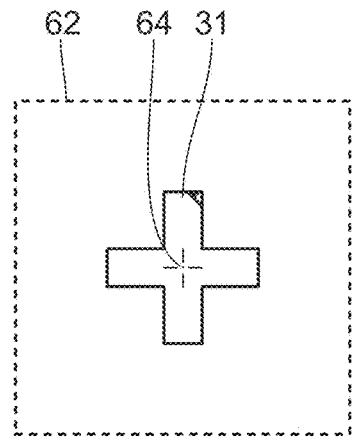
FIGS. 19 to 22 show exemplary illustrations for elucidating the method for determining the accurate position of a defect with the aid of a correlation method.

As is illustrated schematically in FIG. 19, the defect 31 illustrated in the shape of a cross in FIGS. 19 to 22 is situated exactly in the center of the region to be examined (ROI) 62. In this case, the position of the defect 31 corresponds exactly to the center 64 of the region to be examined (ROI) 62. In this case, the position of the defect 31 would already be known.

Figure 20:
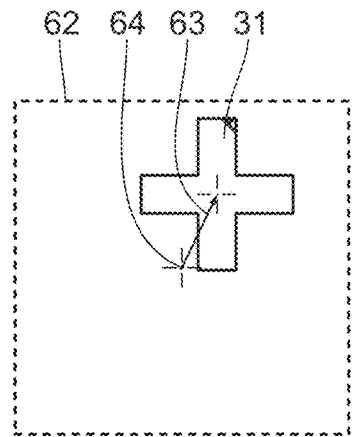
Figure 21:
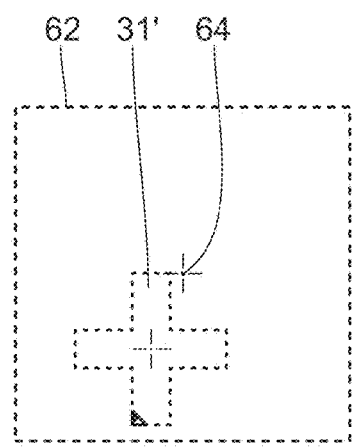
Figure 22:
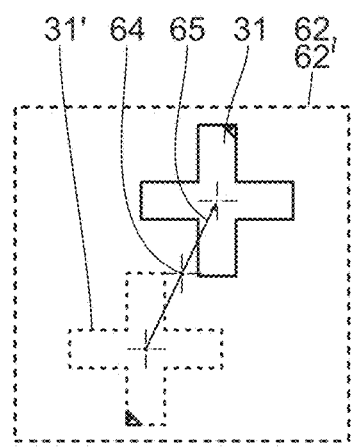

As is illustrated by way of example in FIG. 20, the actual position of the defect 31 can deviate from the expected position by an initially unknown absolute value, illustrated as vector 63 in FIG. 20.

From the initially unknown vector 63 it is possible to determine the precise position of the defect 31 in the coordinate system of the optical unit and thus including the information about the displacement position of the holding device 17 and/or the flexure of the substrate 2 in the substrate coordinate system.

In the individual image analysis 60, the region to be examined (ROI) 62 is then point-mirrored at the center 64. In other words, the region to be examined (ROI) 62 is mirrored in the x- and y-directions. This results in the virtual image—illustrated by way of example in FIG. 21—of the region to be examined (ROI) 62', in particular of the defect 31'.

The actual image of the defect 31 (see FIG. 20) and the virtual image of the defect 31' (see FIG. 21) are then correlated in order to determine a displacement vector 65 between the actual position of the defect 31 and of the mirrored defect 31'. The displacement vector 65 is precisely double the vector 63 that specifies the position of the defect 31 relative to the center 64 of the region to be examined (ROI) 62.

During the positioning of the substrate 2 on the supports 19, the substrate 2 can experience flexure on account of gravitation. The absolute value and the exact course of this flexure can be determined from the mechanical properties of the substrate. Possible values are summarized in the following table.

TABLE 2

| Material | Modulus of elasticity [N/m$^2$] | Poisson ratio | Density [kg/m$^2$] |
|---|---|---|---|
| Quartz | 73800 | 0.17 | 2210 |
| ULE glass | 76600 | 0.17 | 2210 |

Further geometrical data of the substrate 2 and of the layers 26, 27, 28, 29 and 30 are summarized in terms of the main points in table 3:

TABLE 3

| Substrate | |
|---|---|
| Length | 152 mm |
| Width | 152 mm |
| Thickness | 6.35 mm |
| Multilayer 26 | At least 40 Si—Mo double plies |
| Thickness of the individual silicon plies | 4.1 nm |
| Thickness of the individual molybdenum plies | 2.8 mm |
| Thickness of the covering layer 27 | 2.5 nm |
| Thickness of the absorber layer 28 | 44 nm to 108 nm |
| Thickness of the rear-side layer 30 | 20 nm to 200 nm |

The flexure of the substrate 2 can also be determined with the aid of a simulation, in particular with the aid of a finite elements method.

Figure 23:
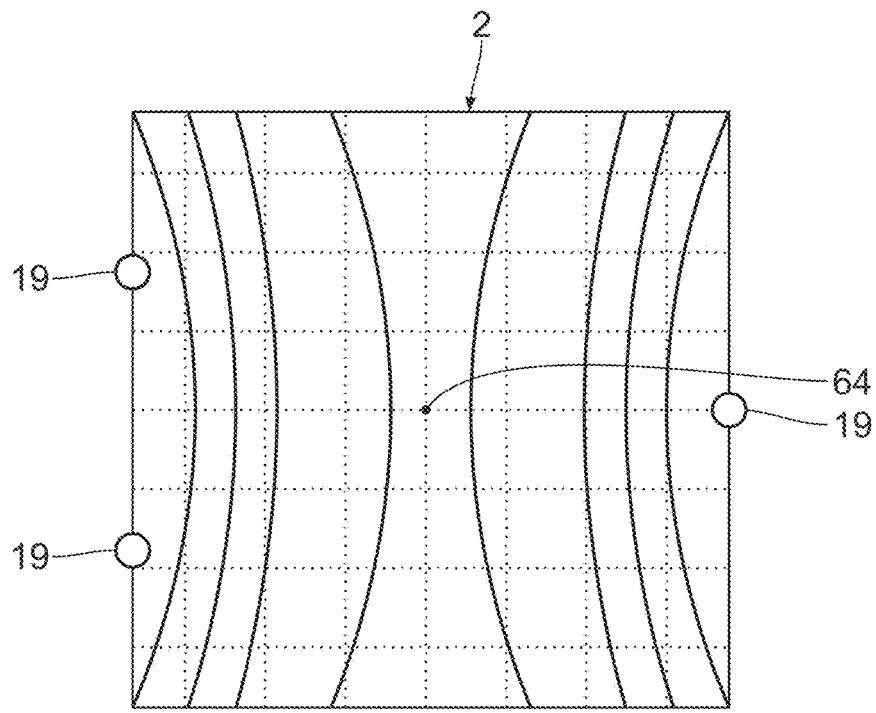
FIG. 23 shows a schematic illustration of the result of an FEM simulation for determining the z-flexure of the substrate.
Figure 24:
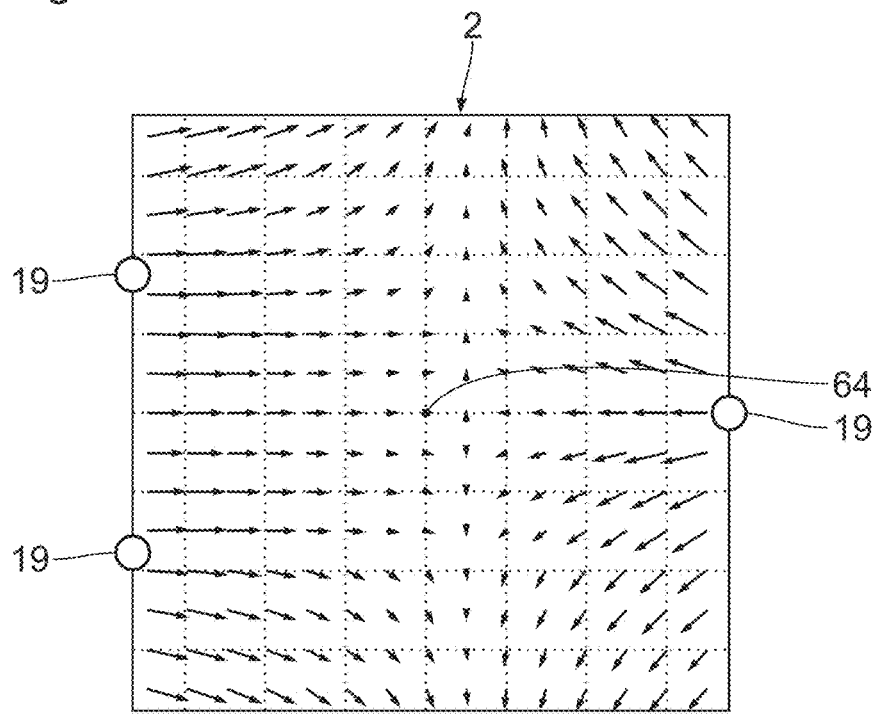
FIG. 24 shows a corresponding illustration of the xy-distortion in accordance with the FEM simulation.
Figure 25:
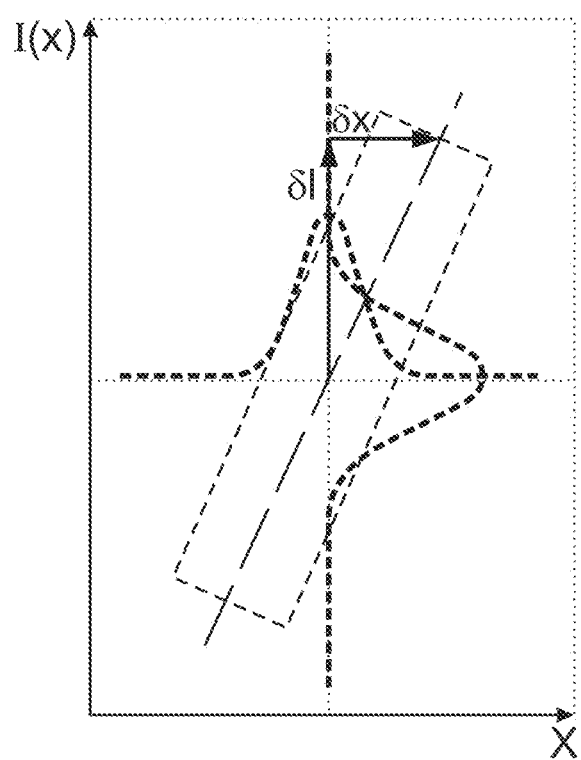
FIG. 25 shows a schematic illustration of the relationship between the image noise δI and position noise δx of the detection.

The result of the flexure is illustrated by way of example in FIGS. 23 and 24. In particular, the z-flexure field of the substrate 2 arranged on the supports 19 is illustrated in gray-shade levels in FIG. 23. The flexure model can be interpolated for any arbitrary (x, y) measurement point in order to obtain the corresponding value for the z-flexure at the location (x, y).

FIG. 24 illustrates in particular the xy-flexure field, that is to say the xy-distortion corresponding to the flexure. The distortion can be interpolated for any arbitrary (x, y) point. The maximum xy-distortion is 47 nm. It is therefore essential to take account of the flexure of the substrate 2, in the image analysis 47, in particular in the transformation between the coordinate system of the apparatus 1 and the coordinate system of the substrate 2.

After the inverse transformation of the position of the defect 31 into the coordinate system of the substrate 2, the accurate position data of the defect 31 are present for the ideal substrate 2, that is to say the substrate 2 having no flexure.

In order to test the method according to the invention, in particular for image capture 54, simulations were carried out. In this case, recourse was had to the simplified construction of the apparatus 1 as illustrated in FIG. 2. For the simulation it is unimportant whether the substrate 2 is analyzed in the reflection mode or in the transmission mode.

For the simulation, the radiation source 4 was modeled as a limited number of discrete point light sources. Each of said point light sources emits a spherical wavefront which propagates coherently through the optical system and leads to an intensity distribution in the image plane which corresponds to the sensor of the CCD camera 14. The intensity distributions of the individual point light sources are summed incoherently in order to simulate a partially coherent image of the radiation source 4.

A numerical aperture of the imaging optical unit 9 of 0.8 and a pupil degree of filling of the illumination pupil of 15% was furthermore assumed. Inter alia the following values were fixed as characteristics of the CCD camera 14: read-out noise: 8 e$^-$; dark current for an integration time of 200 ms: 1.22 e$^-$.

Figure 12:
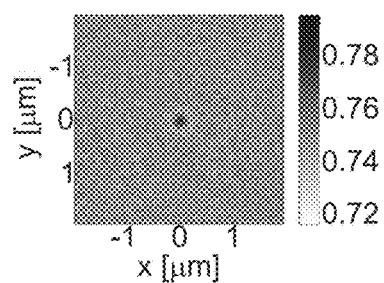
FIGS. 12 to 14 show exemplary illustrations of images of different substrates with a defect (bump) with SEVD 28 nm and height 0.5 nm.
Figure 13:
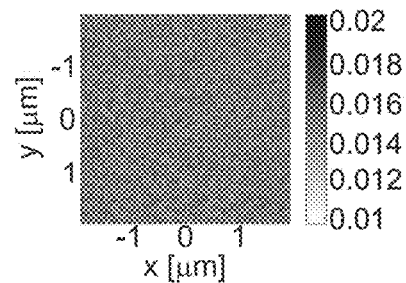

For defects 31 having a spherical equivalent volume diameter (SEVD) of 28 nm and a height of 0.5 nm, the resulting ideal shape for the radiation source 4 is a disc having an inner radius 0, that is to say a circular radiation source 4. Correspondingly, the phase mask 11 is embodied in a circular fashion in this case. The images thus obtained are illustrated by way of example in FIGS. 12 to 14. FIG. 12 illustrates the case where the substrate 2 is analyzed before the absorber layer 28 is applied. The defect 31 is thus localized before the absorber layer 28 is applied, that is to say before the second deposition step 39. FIG. 13 illustrates the case where the substrate 2 is measured after the absorber layer 23 has been applied to the covering layer 27, that is to say after the second deposition step 39. The illustration shows by way of example the case where 98% of the illumination radiation 5 is absorbed, that is to say not reflected, or not transmitted in the transmission mode.

Figure 14:
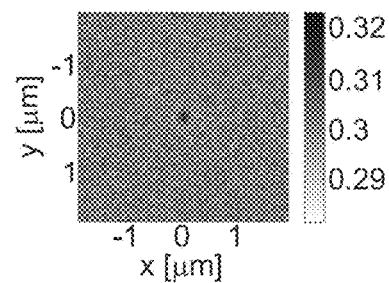

The case illustrated in FIG. 14 corresponds to the case illustrated in FIG. 13, wherein the integration time was lengthened to 4 s. In the case of the images illustrated in FIGS. 12 and 13, the integration time is 200 ms.

The illustrations show in each case a region to be examined (ROI) 62 of 4 μm·4 μm, which is centered at 0.

Figure 3:
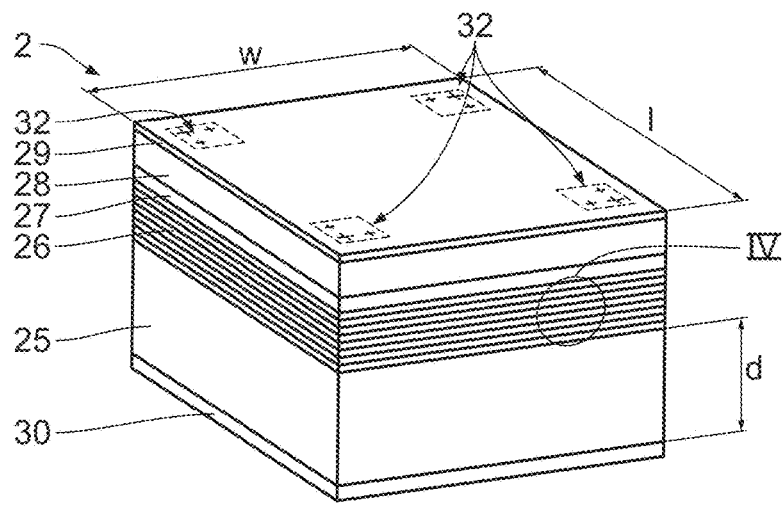

The image contrast-to-noise ratio (cnr) is 8.5 in the case of the imaging illustrated in FIG. 12, 0.2 in the case of the imaging illustrated in FIG. 13 and 3.4 in the case of the imaging illustrated in FIG. 14.

The imagings are in each case normalized in such a way that the image without defects 31 and background noise is completely saturated, that is to say consists of ones, provided that the camera is operated with full capacity.

The total magnification of the phase contrast optical unit, that is to say of the imaging optical unit 9 and of the magnifying optical unit 10, is chosen in each case in such a way that each pixel of the image has a size of (17.5 nm)$^2$.

The defects 31 illustrated in FIGS. 12 to 14 are bumps.

Figure 15:
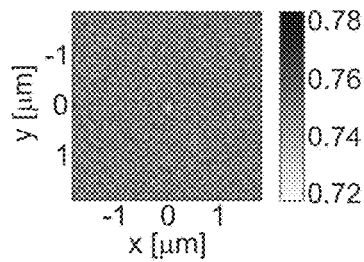
FIG. 15 shows an exemplary illustration of an image of a defect (Pit) with SEVD=18 nm and height 5 nm.
Figure 16:
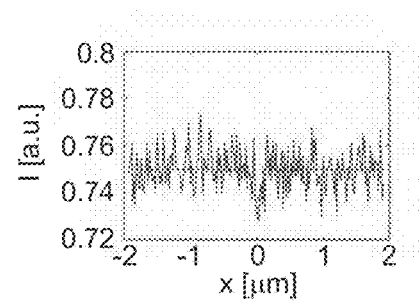
FIG. 16 shows a section along the line XVI-XVI through FIG. 15, FIGS. 17 and 18 show illustrations corresponding to FIGS. 15 and 16 for a defect (Pit) with SEVD=18 nm and height 0.5 nm.

FIG. 15 illustrates an image corresponding to that in FIG. 12, but for a defect 31 in the form of a pit having an SEVD of 18 nm and a depth of 5 nm. The image contrast-to-noise ratio is 3.9. FIG. 16 illustrates a section (y=0) through the image in accordance with FIG. 15. An actual, noisy signal 66 and an ideal, noise-free signal 67 are illustrated. The noise-free signal 67 can be determined for example by a curve fitting to the noisy signal 66.

Figure 17:
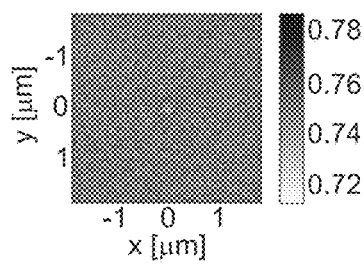
Figure 18:
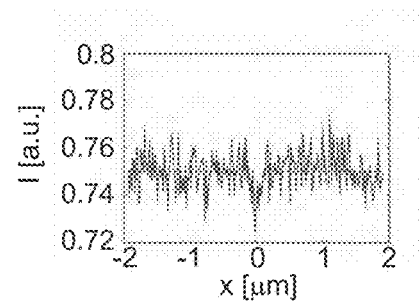

FIGS. 17 and 18 illustrate images corresponding to those in FIGS. 15 and 16, but for a defect 31 having an SEVD of 18 nm and a depth of 0.5 nm. The image contrast-to-noise ratio is 3.3. In this case, too, the defect 31 is clearly identifiable and localizable.

As is directly evident qualitatively from a comparison of the images in accordance with FIGS. 12 to 14 and 15 to 18, from said images it is possible to draw a distinction directly between defects 31 in the form of bumps and pits. In particular, a single focal position is sufficient for this distinction. In particular, no focus stagger is required.

In order to show the applicability of the image analysis 47 for localizing defects 31 having different shapes, in particular bumps and pits, a Monte Carlo simulation was carried out. Defects 31 having three different sizes were simulated in this case. The simulated images were superimposed with the camera noise described above. The image stack contained in each case seven images with a defocus difference of 30 nm between adjacent images. 100 Simulations with stochastic noise were carried out for each configuration. From these data, as a measure of the reliability, in particular the repeatability, the triple standard deviation was determined by use of symmetry correlation. The results are summarized in the following table. The values in each case represent the triple standard deviation [nm] in the x- and y-directions. For defects in the form of a pit and in the form of a bump

TABLE 4

| triple standard deviation [nm] | | | | | |
|---|---|---|---|---|---|
| Defect size (SEVD; height) | | | | | |
| 40 nm; 5 nm | | 40 nm; 0.5 nm | | 28 nm; 0.5 nm | |
| X | Y | X | Y | X | Y |
| Pit | 0.90 | 0.96 | 4.50 | 4.78 | 5.21 | 5.36 |
| Bump | 1.14 | 1.04 | 4.94 | 4.97 | 5.46 | 5.47 |

These results prove that the method leads to a reliability, characterized by the triple standard deviation, of far better than 10 nm, in particular better than 6 nm. It thus leads to a considerable improvement in the localization of defects 31 on substrates 2 for producing EUV masks.

Details of one preferred method for image analysis 47 are described below with reference to FIGS. 25 to 28.

In the individual image analysis 60, in particular in the registration measurement of microscope images, the edge steepness of the imaged structures is of crucial importance for the accuracy and reproducibility of the measurement. By way of the edge steepness m, image noise $\delta I$ always present in the camera image is translated into position noise $\delta x$ of the detection, specifically according to the formula $\delta x = \delta I/m$ (see FIG. 25).

Figure 26:
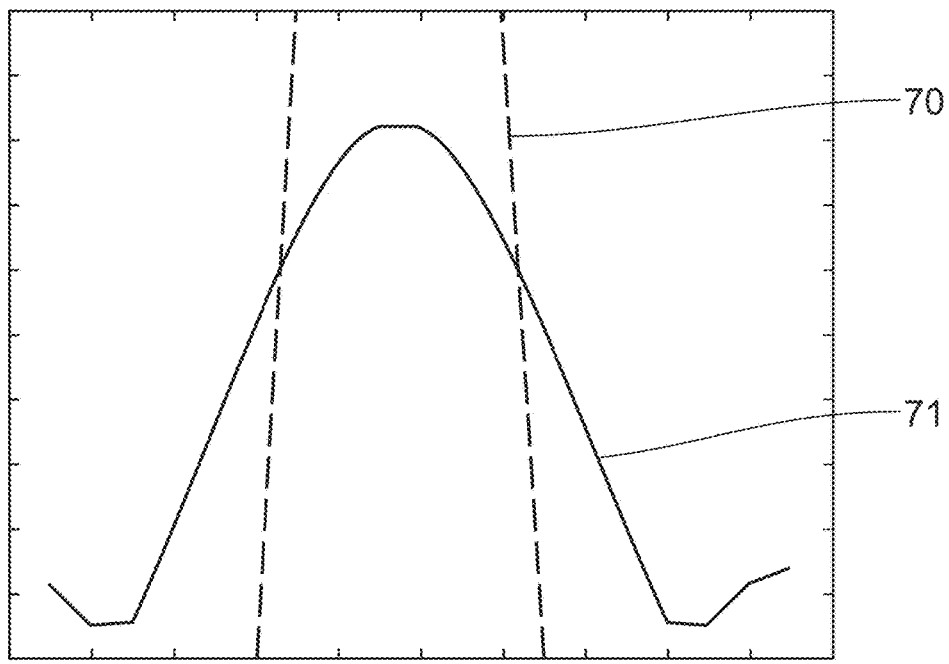
FIG. 26 shows a schematic illustration for comparing the edge steepness of an object amplitude and an image amplitude of the same object.

This is the case in particular for small structures, in particular for structures which exhibit a low edge steepness on account of diffraction effects. FIG. 26 illustrates by way of example a comparison of an object amplitude 70 with an image amplitude 71. The illustrated amplitudes 70, 71 are the amplitudes 70, 71 of an object having a linewidth of 125 nm with coherent illumination with a wavelength of $\lambda=193$ nm and a numerical aperture NA=0.6. The reduced edge steepness of the image amplitude 71 in comparison with the object amplitude 70 is visible.

According to the invention, it has been recognized that phase images have the advantage that their edge steepness, in particular phase jump edges, is significantly steeper than that of intensity images. This can advantageously be utilized in the image analysis 47.

Figure 27:
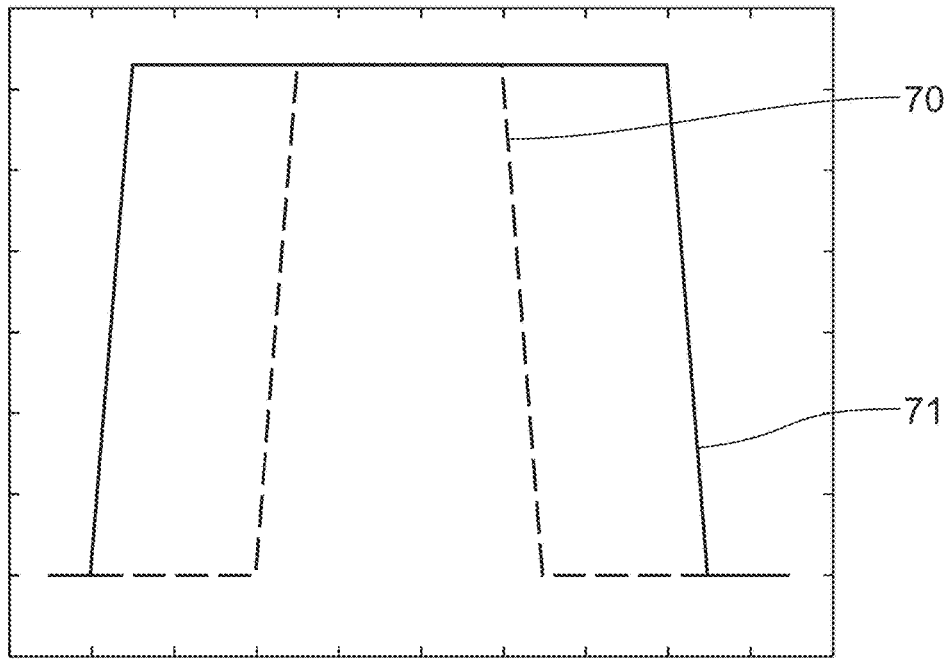
FIG. 27 shows a schematic illustration corresponding to FIG. 26 for comparing the edge steepness of the object phase and the image phase of the same object.

FIG. 27 illustrates by way of example an object phase 72 and an image phase 73 for the same object. The image phase 73 has the same edge steepness as the object phase 72. However, the image phase 73 exhibits a widening of the phase line. This is not a disturbance in the present context.

Figure 28:
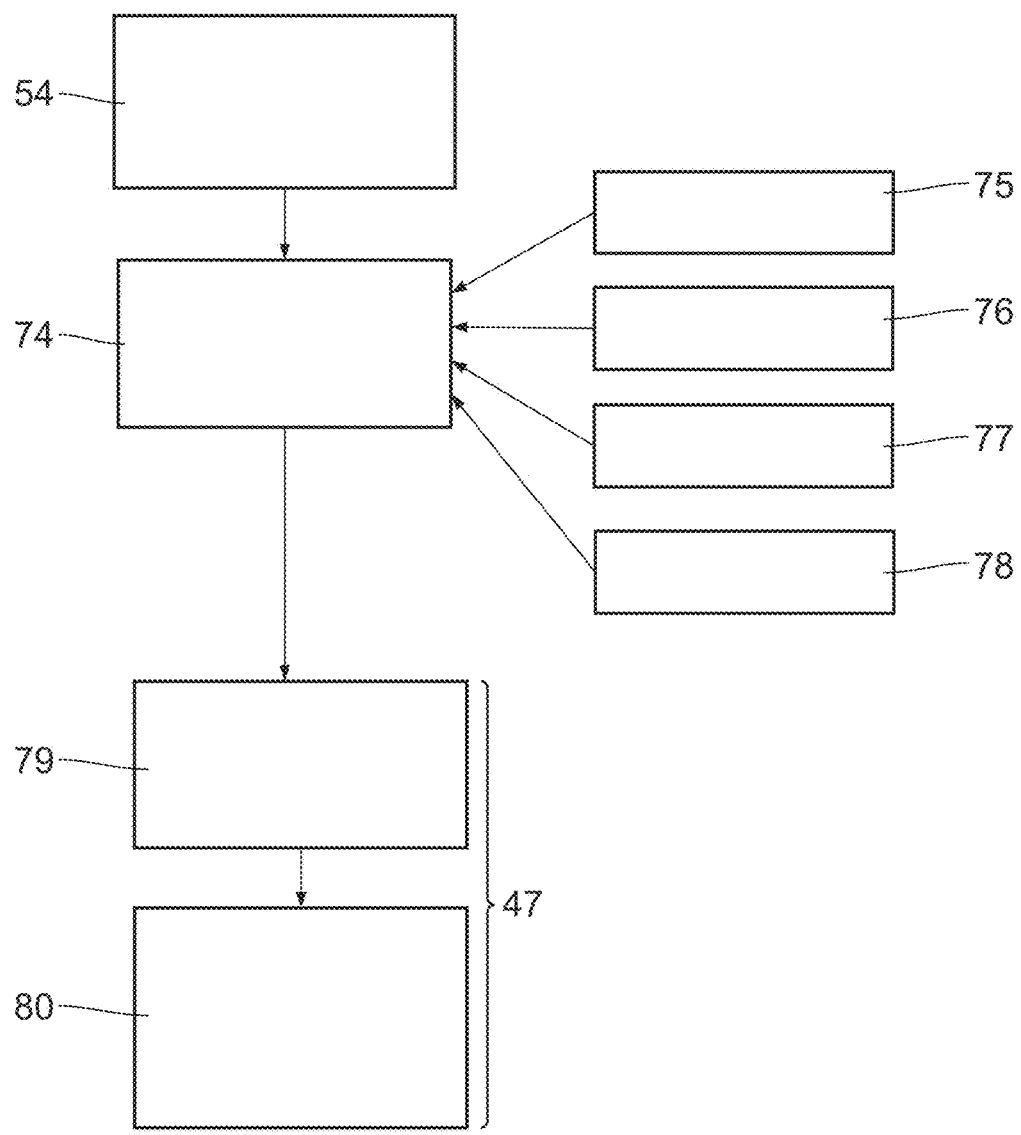
FIG. 28 shows a schematic illustration of the method sequence of a method for the registration measurement of phase images.

In accordance with one advantageous method, the sequence of which is illustrated schematically in FIG. 28, a reconstruction step 74 is provided after the image capture step 54. Said reconstruction step 74 involves reconstructing a phase image from the intensity image recorded during image capture 54.

In the reconstruction step 74, in particular, the image phase is reconstructed. As an alternative thereto, it is possible to determine an equivalence phase in the image plane. In this regard, it has been recognized that the equivalence phase can be used as a basis for a registration measurement in just the same way as the image phase.

Various methods can be provided for the reconstruction step 74. In particular, a method selected from the following list can be provided: phase determination by using an iterative Fourier transformation algorithm 75 (IFTA), in particular by use of a Gerchberg-Saxton algorithm, model-based phase determination 76, methods 77 based on the transport of intensity equation (TIE), and Fourier ptychography 78. Further possibilities for determining the image phase or the equivalence phase in the reconstruction step 74 are likewise possible. The method functions, in principle, for every possibility with which the image phase or the equivalence phase can be determined.

For details of phase determination by use of an iterative Fourier transformation algorithm 75, reference should be made to WO 2008/025 433 A2.

In the model-based phase determination 76, the phase is not determined pixel by pixel, rather the parameters of a model, for example Zernike polynomials, are determined in particular iteratively.

The image analysis 47 comprises the phase image evaluation 79 in this method. It can optionally also comprise an intensity image evaluation 80 and in particular a comparison of the results of the phase image evaluation 79 with those of the intensity image evaluation 80. The image evaluations 79, 80 are also referred to as registration measurements.

The method is suitable in particular for coherent illumination. However, for non-coherently illuminated microscope images, too, an image phase or an equivalence phase of the image can be determined by using the method described above.

In this case, too, the phase image has steeper edges than the intensity image.

The phase image evaluation 79 can be carried out by use of threshold methods. For details, reference is made for example to DE 10 2009 015 594 A1. The phase image evaluation 79 can also be carried out with the aid of correlation-based methods. For details, reference should be made to US 2013/0019212 A1 and DE 10 2011 077 296 A1.

Further aspects, advantages and alternatives of the invention are described below in a brief summary. The general details of the corresponding methods correspond to those known from the description above, to which reference is hereby made.

One major advantage of the method according to the invention is that it is significantly faster and more accurate than the methods customary heretofore. This is attributable, in particular, to the fact that with the method according to the invention it suffices, for the purpose of analyzing a defect, to record a single image thereof. The number of images required in an image stack can be reduced, in particular. Furthermore, it was able to be shown that it is possible to localize the defects with high accuracy. In particular, it is possible not just to make statements in respect of whether a substrate has a defect, but to specify accurately in what region, that is to say at what position, said defect is localized.

As a result, it is possible to compensate for the defect for later applications by using suitable processing steps.

Figure 29:
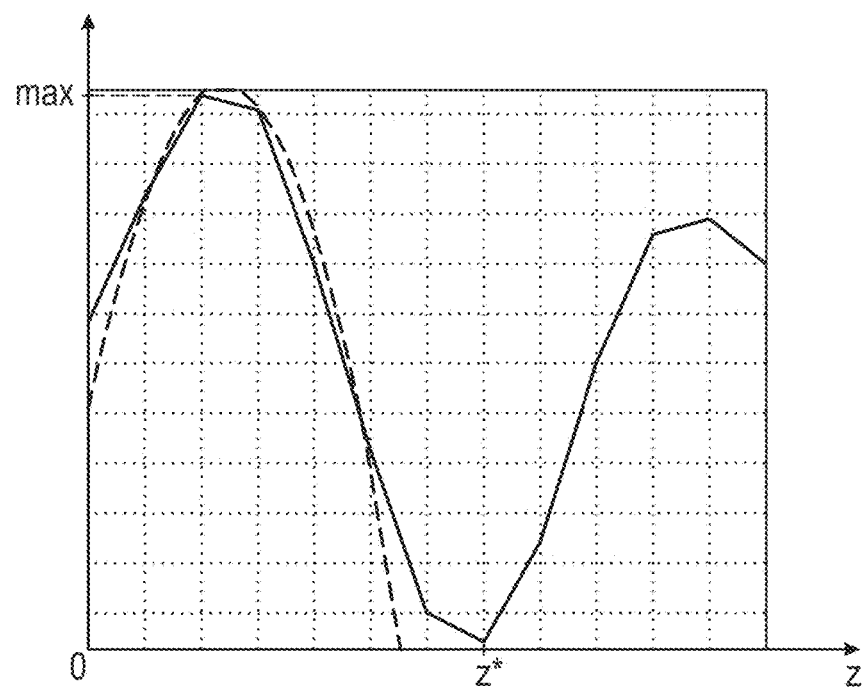
FIG. 29 shows an exemplary illustration of the contrast of an actually recorded image of a test defect as a function of the defocus position z when using a system without a phase mask.
Figure 30:
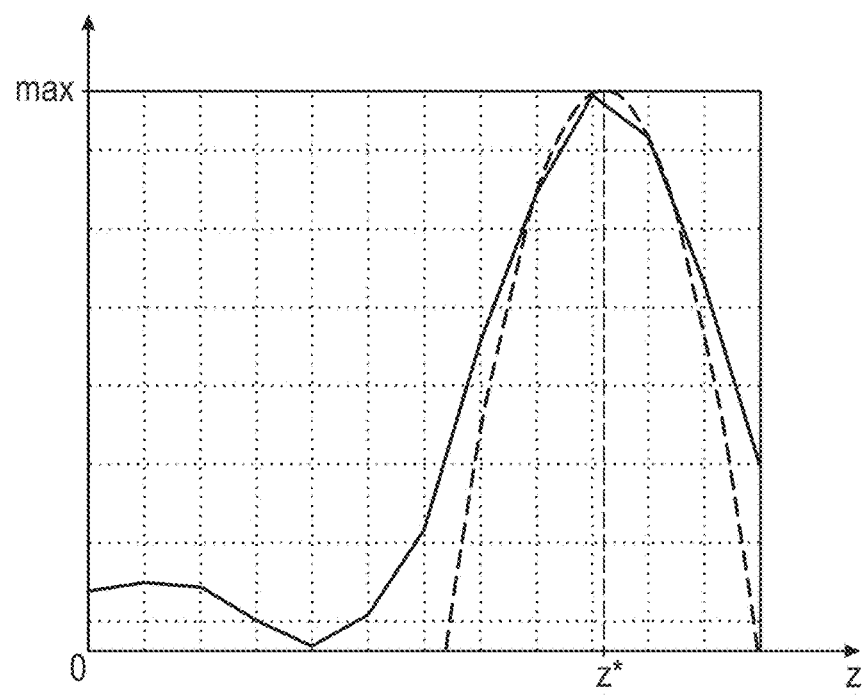
FIG. 30 shows an illustration corresponding to FIG. 29 when using a system with a phase mask.

The applicability and the advantages of the method according to the invention were checked and confirmed both by simulations and on the basis of measurement series carried out with the aid of test structures. FIGS. 29 and 30 illustrate by way of example the dependence of the contrast on the defocus position without the phase mask 11 (FIG. 29) and with the phase mask 11 (FIG. 30). The curves depicted arose from actual measurements of a phase test defect. The figures additionally illustrate in a dashed manner parabolic fits in the region of the measured maximum of the curves. Corresponding curves also arose from Monte Carlo simulations of noisy camera images of typical defects having different sizes and having different phase errors. The results can therefore be regarded as very robust.

It can be emphasized in summary that the method according to the invention, in particular the use of the phase mask 11, led to an in most cases improved accuracy and/or repeatability of the analysis of phase defects, in particular having a defect size in the range of less than 500 nm, in particular less than 300 nm, in particular less than 200 nm, and a phase error of less than 45°, in particular in the range of 5° to 30°, in particular in the range of 10° to 20°.

As can be gathered by way of example from FIGS. 29 and 30, the images of a defect in the best focal position $z^*$ for the case where no phase mask 11 is used have a contrast of 0 (see FIG. 29). When the phase mask 11 is used (see FIG. 30), no contrast inversion occurs. In this case, the contrast of the phase image in the best focal position $z^*$ is different than 0. The contrast can have a maximum, in particular, in the best focal position $z^*$. By using the method according to the invention, in particular by using the phase mask 11, it is therefore possible to examine the phase defects in the best focal position $z^*$. The number of required images of the defocus stack can be reduced as a result. It is possible, in particular, to analyze the defects on the basis of a single image, in particular an image recorded in the best focal position $z^*$. This leads to a considerable time saving.

Furthermore, by using the simulations and test measurements it was possible to confirm that the reliability (triple standard deviation, "3σ repeatability") could be improved to values of less than 5 nm with the aid of the method according to the invention. The measured reliability was at values of less than <1 nm in the case of more than 80% of the actually measured test defects.

What is claimed is:

1. A method for localizing defects on substrates for producing optical components of a microlithographic EUV projection exposure apparatus, on substrates for EUV lithography masks or on EUV lithography masks, comprising the following steps:
provision steps for providing
a substrate to be examined,
an illumination device for illuminating the substrate to be examined with illumination radiation having a wavelength in the range of 100 nm to 300 nm,
a phase contrast optical unit for examining the substrate to be examined, and
a sensor device for detecting illumination radiation,
preparation steps for preparing the inspection of the substrate to be examined, and
examination steps for examining the substrate comprising capturing at least one image of the substrate, and
analysis and/or aftertreatment steps,
wherein the phase contrast optical unit comprises a phase mask and a stop,
wherein the geometrical embodiment of the phase mask and that of the stop are adapted to one another,
wherein the sensor device is arranged in the beam path downstream of the phase mask, and
wherein the examination steps comprise detecting a phase shift, brought about by the substrate, of the illumination radiation by use of the sensor device.

2. The method as claimed in claim 1, wherein the preparation steps comprise determining a positioning of the substrate in a coordinate system of the phase contrast optical unit, wherein predefined bearing points of a positioning device and/or measurement marks on the substrate serve as reference points.

3. The method as claimed in claim 1, wherein the examination steps comprise predefining a region to be examined on the substrate wherein the region to be examined is predefined with an accuracy that is more precise than a diameter of a field of view of the phase contrast optical unit.

4. The method as claimed in claim 1, wherein the substrate is displaced by use of a positioning device before the at least one image is recorded.

5. The method as claimed in claim 1, wherein the examination steps comprise an image capture with recording of an image stack having at least one intrafocal image and at least one extrafocal image.

6. The method as claimed in claim 1, wherein a single image of the substrate is captured for the purpose of examining the substrate.

7. The method as claimed in claim 1, wherein the analysis and/or aftertreatment steps comprise determining a best focal position.

8. The method as claimed in claim 1, wherein the analysis and/or aftertreatment steps comprise a two-stage method in which, in a first stage, a defect position is determined for each image of an image stack and in which, in a second stage, the defect positions of the images are adapted to a best focal position.

9. The method as claimed in claim 1, wherein a position of the defect in a substrate coordinate system is determined with an accuracy of better than 100 nm.

10. The method as claimed in claim 1, wherein the substrate has an absorber layer when the examination steps are carried out.

11. The method as claimed in claim 1, wherein the analysis and/or aftertreatment steps comprise a reconstruction step for determining a phase image and a subsequent phase image evaluation.

12. A method for producing EUV lithography masks comprising the following steps:
providing a substrate for an EUV lithography mask,
inspecting the substrate in order to localize defects by using the method of claim 1,
structuring the substrate with a structure,
wherein the structure is chosen and/or aligned in such a way that defects on the substrate are covered by an absorber layer.

13. The method as claimed in claim 12, wherein inspecting the substrate in order to localize defects is carried out after applying the absorber layer.

14. An apparatus for localizing defects on substrates and configured to perform the provision, preparation, and examination steps of claim 1, the apparatus comprising
an illumination system for illuminating a substrate to be examined with illumination radiation having a wavelength in the range of 100 nm to 300 nm, and
a phase contrast optical unit for imaging the substrate to be examined,
wherein the phase contrast optical unit has a phase mask and a stop, wherein the phase mask is adapted to a distribution of the illumination radiation in an entrance pupil of the phase contrast optical unit, and wherein the geometrical embodiment of the phase mask and that of the stop are adapted to one another.

15. The apparatus of claim 14, wherein the apparatus is configured to perform preparation steps that comprise determining a positioning of the substrate in a coordinate system of the phase contrast optical unit, wherein predefined bearing points of a positioning device and/or measurement marks on the substrate serve as reference points.

16. The apparatus of claim 14, wherein the apparatus is configured to perform examination steps that comprise predefining a region to be examined on the substrate wherein the region to be examined is predefined with an accuracy that is more precise than a diameter of a field of view of the phase contrast optical unit.

17. The apparatus of claim 14, wherein the substrate is displaced by use of a positioning device before the at least one image is recorded.

18. The apparatus of claim 14, wherein the apparatus is configured to perform examination steps that comprise an image capture with recording of an image stack having at least one intrafocal image and at least one extrafocal image.

19. The apparatus of claim 14, wherein the apparatus is configured to capture a single image of the substrate for the purpose of examining the substrate.

20. The apparatus of claim 14, wherein the sensor device is arranged in the beam path downstream of the phase mask, and the apparatus is configured to detect a phase shift, brought about by the substrate, of the illumination radiation by use of the sensor device.

* * * * *